US010238704B2

(12) United States Patent
Agisim et al.

(10) Patent No.: US 10,238,704 B2
(45) Date of Patent: Mar. 26, 2019

(54) PRE MOISTENED WIPES FOR USE IN TREATING ANAL RECTAL IRRITATIONS AND DISORDERS

(71) Applicant: Pfizer Inc, New York, NY (US)

(72) Inventors: Gary Robert Agisim, Henrico, VA (US); Robert Alan Friedline, Richmond, VA (US); Richard John Kenny, Glen Allen, VA (US)

(73) Assignee: Pfizer Inc., New York, NY (US)

( * ) Notice: Subject to any disclaimer, the term of this patent is extended or adjusted under 35 U.S.C. 154(b) by 812 days.

(21) Appl. No.: 14/572,491

(22) Filed: Dec. 16, 2014

(65) Prior Publication Data

US 2015/0174182 A1   Jun. 25, 2015

Related U.S. Application Data

(60) Provisional application No. 61/919,123, filed on Dec. 20, 2013.

(51) Int. Cl.
| | |
|---|---|
| *A61K 36/185* | (2006.01) |
| *A61K 47/10* | (2017.01) |
| *A61K 47/46* | (2006.01) |
| *A61K 8/34* | (2006.01) |
| *A61K 8/44* | (2006.01) |
| *A61K 8/67* | (2006.01) |
| *A61K 8/86* | (2006.01) |
| *A61Q 19/10* | (2006.01) |
| *A61K 8/97* | (2017.01) |
| *A61K 8/02* | (2006.01) |

(52) U.S. Cl.
CPC .......... *A61K 36/185* (2013.01); *A61K 8/0208* (2013.01); *A61K 8/345* (2013.01); *A61K 8/44* (2013.01); *A61K 8/678* (2013.01); *A61K 8/86* (2013.01); *A61K 8/97* (2013.01); *A61K 47/10* (2013.01); *A61K 47/46* (2013.01); *A61Q 19/10* (2013.01)

(58) Field of Classification Search
CPC ....... A61K 36/28; A61K 36/42; A61K 36/886
USPC ......................................... 424/744, 758, 776
See application file for complete search history.

(56) References Cited

U.S. PATENT DOCUMENTS

| | | | |
|---|---|---|---|
| 4,100,324 | A | 7/1978 | Anderson et al. |
| 6,896,890 | B2 | 5/2005 | Singh et al. |
| 2004/0151763 | A1 | 8/2004 | Durden |
| 2007/0184009 | A1 | 8/2007 | Rogers et al. |
| 2009/0123397 | A1* | 5/2009 | Seal ...................... A61K 8/345 424/59 |

FOREIGN PATENT DOCUMENTS

WO   2002/024165 A2   3/2002

OTHER PUBLICATIONS

Mintel Complete Cleansing wipes (Published Oct. 2010) (Year: 2010).*
PubMed.gov (Int. Journal of Toxicology, 2008;27 Supplemental 4:1-82 doi: 10.1080/1091581080-2548359) (Year: 2008).*
Mitel Sensitive Skin Moist Wipes (Published Oct. 2007) (Year: 2007).*
Khatiashvili N S et al: "Lipids from *Sterculia platanifolia* and *Hamamelis virginiana* seeds", Medicinal & Aromatic Plants Abstracts, Scientific Publishers, Scientific Publishers, New Delhi—India, vol. 30, No. 1, Feb. 1, 2008 (Feb. 1, 2008), XP018023723, ISSN: 0250-4367.
"Witch Hazel with 14% alcohol", Mar. 3, 2015 (Mar. 3, 2015), p. 2pp, XP007923030, Retrieved from the Internet: URL:http://www.whazel.com/sites/default/files/American_Distilling_SELLSHEET_W-H_14_6-10.pdf [retrieved on Mar. 3, 2015].
Anonymous: "Witch Hazel, *Hamamelis virginiana*, witch hazel photos and article by Steven Foster", Dec. 16, 2013 (Dec. 16, 2013), XP055173542, Retrieved from the Internet: URL:https://web.archive.org/web/20131216095902/http://www.stevenfoster.com/education/monograph/witchhazel.html [retrieved on Mar. 4, 2015].
"Amazon.com: witch hazel", Mar. 2, 2015 (Mar. 2, 2015), p. 4pp, XP007923031, Retrieved from the Internet: URL:http://www.amazon.com/s/ref=sr_nr_n_13?fst=as%3Aoff&rh=n%3A3763781%2Ck%3Awitch+hazel&keywords=witch+hazel&ie=UTF8&qid=1425293049&rnid=2941120011 [retrieved on Mar. 2, 2015].
"Preparation H Medicated Hemorrhoidal Wipes With Witch Hazel 2 Pack Walgreens", Mar. 3, 2015 (Mar. 3, 2015), p. 9pp, XP007923032, Retrieved from the Internet: URL:http://www.drugs.com/otc/162434/preparation-h-medicated-wipes-for-women.html?printable=1 [retrieved on Mar. 3, 2015].
Database GNPD [Online] MINTEL; Nov. 1, 2011 (Nov. 1, 2011), "Feminine Care Cleansing Cloth" XP002736733, Database accession No. 1658845.
Database GNPD [Online] MINTEL; Apr. 1, 2011 (Apr. 1, 2011), "Soft Nose Wipes", XP002736734, Database accession No. 1520918.
Database GNPD [Online] MINTEL; Oct. 1, 2010 (Oct. 1, 2010), "Complete Cleansing Wipes", XP002736735, Database accession No. 1421538.
Database GNPD [Online] MINTEL; Aug. 1, 2014 (Aug. 1, 2014), "Intimate Wet Wipes", XP002736736, Database accession No. 2606325.
Database GNPD [Online] MINTEL; Jun. 1, 2009 (Jun. 1, 2009), "Flushable Personal Hygiene Wipes", XP002736737, Database accession No. 1120785.
Database GNPD [Online] MINTEL; Oct. 1, 2007 (Oct. 1, 2007), "Sensitive Skin Moist Wipes", XP002736738, Database accession No. 794861.
Database GNPD [Online] MINTEL; Jan. 1, 2014 (Jan. 1, 2014), "Feminine Hygiene Wet Tissues",XP002736739, Database accession No. 2294120.

(Continued)

*Primary Examiner* — Christopher R Tate
*Assistant Examiner* — Deborah A Davis
(74) *Attorney, Agent, or Firm* — Paula K. Davis; Jeffrey M. Gold

(57) ABSTRACT

Many people who suffer from anal rectal discomfort and disorders need fibrous sheet materials which are pre-moistened with a solution for improved cleansing without excessive skin irritation. The invention particularly concerns wet wipes, such as anal-rectal wipes, which comprises a solution comprising hamamelis water or witch hazel, to effectively treat anal-rectal disorders.

18 Claims, No Drawings

(56) References Cited

OTHER PUBLICATIONS

"Lipex(R)102 E75 Lipex(R)203 E70", Aug. 2008 (Aug. 2008), p. 1, XP007923034, URL:http://www.aak.com/Global/Products/Beauty%20and%20personal%20care/Surfactants/aak-lfc_lipex_102-203_E75-E70_0808.pdf [retrieved-on Mar. 3, 2015].
Anonymous: "Ingredient Showdown: Cocamidopropyl Betaine and Betaine", May 12, 2014 (May 12, 2014), XP055173609, URL:http://www.naturallycurly.com/curlreading/ingredients/ingredient-showdown-cocamidopropyl-betaine-and-betaine/ [retrieved on Mar. 4, 2015].
Tucks® Take Alongs® Medicated Towelettes, https://web.archive.org/web/20110717112101/http://www.tucksbrand.com/take-alongs-medicated-towelettes, Jul. 17, 2011.
Witch Hazel+Shea Butter=Perfect!, http://badgerandblade.com/vb/showthread.php/337710WitchHazelSheaButterPerfect!, Mar. 17, 2013.

* cited by examiner

PRE MOISTENED WIPES FOR USE IN TREATING ANAL RECTAL IRRITATIONS AND DISORDERS

FIELD OF INVENTION

The present invention relates to fibrous sheet materials which are premoistened with a solution for improved cleansing without excessive skin irritation. The invention particularly concerns wet wipes, such as anal-rectal wipes, which include hamamelis water or witch hazel, which is suitable for a woman's anal-rectal and perineal area. The wet wipe should comprise an effective cleansing solution but also be non-irritating and convey a sense and smell of freshness.

BACKGROUND OF THE INVENTION

Wet wipes are well known commercial consumer products which have been available in many forms. Perhaps the most common form of wet wipes has been a stack of moistened sheets which have been packaged in a plastic container. The wet wipes have been made from a variety of materials which have been moistened with a variety of suitable wiping solutions. Typically, the wet wipes have been available in either folded or unfolded configurations. For example, stacks of wet wipes have been available wherein each of the wet wipes in the stack has been arranged in a folded configuration such as a c-folded, z-folded or quarter-folded configuration as are well known to those skilled in the art. Each folded wet wipe has also been interfolded with the wet wipes immediately above and below in the stack of wet wipes. In an alternative configuration, the wet wipes have been in the form of continuous webs of material which include perforations to separate the individual wet wipes and which are wound into rolls and packaged in plastic containers. Such wet wipes have been used for baby wipes, hand wipes, household cleaning wipes, industrial wipes and the like.

The solutions incorporated into conventional wet wipes have usually included a number of ingredients intended to enhance or impart particular properties to the wipe. These properties have related to, for example, cleaning efficacy, fragrance, medication, reduced irritation, skin health, aesthetics of the product and the like. For baby wipes, a solution providing a gentle soothing feeling without excessive irritation or foam while maintaining cleaning and antimicrobial efficacy is highly desirable for product performance. Suitable ingredients used to provide such properties have included water, emollients, surfactants, preservatives, chelating agents, pH buffers or combinations thereof. The solutions have also contained lotions and/or medicaments.

However, the conventional solutions and, in particular, the surfactants in such solutions for wet wipes have not been completely satisfactory. For example, to reduce the level of skin irritation, conventional wet wipe solutions have included amphoteric surfactants which generally cause little or no skin irritation. Such amphoteric surfactants have included sodium cocoamphoacetate and disodium cocoamphodiacetate. However, such amphoteric surfactants have typically not exhibited the high levels of cleaning efficacy associated with other surfactants such as anionic surfactants. Such amphoteric surfactants typically have also not provided the optimum silky feeling to the skin which is desired by consumers, particularly female consumers.

On the other hand, anionic surfactants, while exhibiting such cleaning efficacy, have generally caused excessive skin irritation such as dryness and scaling and, as a result, have not been suitable for use in wet wipe applications. The high level of skin irritation caused by such surfactants is particularly undesirable in female anal-rectal and perineal area medicament applications due to the tenderness of the vaginal and anal skin. Moreover, most anionic surfactants are suitable for detergent compositions due to their high levels of foaming and detersive activity. However, such foaming is generally undesirable in wet wipe applications and, in particular, in anal-rectal medicament wipe applications. Consumers who use wet wipes prefer that the solution from the wet wipes not leave any soapy or bubbly residue on the surface of the skin since the solution is usually not wiped off the skin after the wet wipe is used.

For a woman's anal-rectal and perineal area medicament wipes, a solution providing a gentle soothing feeling without excessive irritation or foam while maintaining cleaning and antimicrobial efficacy is highly desirable for product performance. The solution must be effective but also non-irritating and convey a sense and smell of freshness. Baby wipes are more for mild and effective cleansing whereas the novel wipes disclosed in the present application are designed for mild and effective cleansing but also soothing relief.

Accordingly, it remains desirable to provide solutions for wet wipes which include surfactants which exhibit improved cleaning efficacy while not causing excessive skin irritation or foaming.

It is highly desirable to use a surfactant that is specifically designed for cleansing the delicate and sensitive skin of the female anal-rectal and perineal area. The betaine class of surfactants are desirable because they provide effective cleansing, generally do not foam and are known for their mildness characteristics.

SUMMARY OF THE INVENTION

In response to the difficulties and problems discussed above, new wet wipes which have improved solutions for application to a woman's anal-rectal and perineal area have been discovered.

In one aspect, the present invention relates to a wet wipe comprising a fibrous sheet material and a non-oily aqueous-based solution which comprises:

a) from about 10 to about 50 percent witch hazel;
b) from about 0.01 to about 2 percent of at least one emulsifier; and
c) from about 0.01 to about 0.20 percent of at least one emollient;

wherein the weight percent is based on a total weight of said solution.

In another aspect, the present invention relates to a wet wipe comprising a fibrous sheet material and a non-oily aqueous-based solution which comprises:

a.) about 20 weight percent witch hazel;
b.) about 9 weight percent glycerin;
c.) about 5 weight percent propylene glycol;
d.) about 1.5 weight percent ethoxylated shea butter;
e.) about 0.2 weight percent cucumber extract;
f.) about 0.2 weight percent chamomile extract;
g.) about 0.2 weight percent diazolidinyl urea;
h.) about 0.2 weight percent fragrance;
i.) about 0.2 weight percent methylparaben;
j.) about 0.1 weight percent capryl/capramidopropyl betaine;
k.) about 0.1 weight percent aloe vera;
l.) about 0.1 weight percent vitamin E acetate;
m.) about 0.09 weight percent citric acid;
n.) about 0.09 weight percent sodium citrate;

o.) about 0.05 weight percent edetate disodium; and
p.) about 0.05 weight percent propylparaben;
q.) about 63 weight percent added purified water;
wherein the weight percent is based on a total weight of said solution.

In yet another aspect, the present invention relates to a method of using a wet wipe made in accordance with the wet wipe described above comprising using the wet wipe with the solution contained thereon to wipe a human's skin and leaving a solution deposited by using the wet wipe on the human's skin after wiping is completed.

The present invention, in its various aspects, advantageously relates to wet wipes for application to a woman's anal-rectal and perineal area, which, when compared to conventional wet wipes, have improved cleaning efficacy without excessive skin irritation or foaming and convey a sense and smell of freshness. Moreover, the present invention provides solutions for wet wipes which leave a lubricious, silky feeling to the skin during and after application.

DETAILED DESCRIPTION OF THE INVENTION

The present invention relates to fibrous materials and, in particular, wet wipes which have a multi-component preservation system that is appropriate for a multiple-use-packaged-product for the anal/peri-anal area. The wet wipes comprise a mild surfactant to promote cleaning and provide soothing relief to the irritated area and is appropriate for potentially irritated peri-anal tissues. The wet wipes of the present invention can be used for anal rectal disorders, such as hemorrhoids and the like. Such wet wipes are generally folded and arranged in a stacked configuration inside a suitable container for consumer sale.

Materials suitable for such wet wipes are well known to those skilled in the art. The wet wipes are typically made from fibrous sheet materials which may be woven or nonwoven. For example, the wet wipes of the present invention may include nonwoven fibrous sheet materials which include melt blown, coform, air-laid, bonded-carded web materials, hydro-entangled materials, combinations thereof and the like. Such materials can comprise synthetic or natural fibers or combinations thereof. Typically, the wet wipes define a basis weight of from about 25 to about 120 grams per square meter and desirably from about 40 to about 90 grams per square meter.

The wet wipes of the present invention may comprise a coform base sheet of polymeric microfibers and cellulosic fibers having a basis weight of from about 60 to about 80 grams per square meter and desirably about 75 grams per square meter. Such coform base sheets are manufactured generally as described in U.S. Pat. No. 4,100,324 to Anderson et al. which issued Jul. 11, 1978, and which is herein incorporated by reference. Typically, such coform base sheets comprise a gas-formed matrix of thermoplastic polymeric melt blown microfibers, such as, for example, polypropylene microfibers, and cellulosic fibers, such as, for example, wood pulp fibers.

Most preferably, the wet wipes of the present invention are commercially available Grade SX-810® nonwoven material sold by Ahlstrom Green Bay Inc. of Green Bay, Wis.

Alternatively, the wet wipes of the present invention can comprise a composite which includes multiple layers of materials. For example, the wet wipes may include a three layer composite which includes an elastomeric film or melt blown layer between two coform layers as described above. In such a configuration, the coform layers may define a basis weight of from about 15 to about 30 grams per square meter and the elastomeric layer may include a film material such as a polyethylene metallocene film.

The individual wet wipes are generally arranged in a folded configuration. Such folded configurations are well known to those skilled in the art and include c-folded, z-folded, quarter-folded configurations and the like. Each wet wipe may also be interfolded with the wet wipes immediately above and below in the stack of wet wipes. The wet wipes generally define an unfolded width and an unfolded length. The wet wipes may have any suitable unfolded width and length. For example, the wet wipes may have an unfolded length of from about 2.0 to about 80.0 centimeters and an unfolded width of from about 2.0 to about 80.0 centimeters.

The wet wipes of the different aspects of the present invention also contain a solution which is absorbed into the wet wipes. The amount of solution contained within each wet wipe may vary depending upon the type of material being used to provide the wet wipe, the type of solution being used, the type of container being used to store the wet wipes, and the desired end use of the wet wipes. Generally, each wet wipe can contain from about 150 to about 600 weight percent and desirably from about 250 to about 450 weight percent solution based on the dry weight of the wipe for improved wiping.

In one aspect of the present invention, the wet wipes are packaged in a stack in a plastic container. In such an container, the preferred ratio of solution to dry weight of the wipe is from about 3.5:1 to about 4.5:1, more preferably from about 3.8:1 to about 4.3:1 and most preferably from about 4:1 solution to wipe based on dry weight of said wet wipe. If the amount of solution is less than the above-identified range, the wet wipe may be too dry and may not adequately perform. If the amount of solution is greater than the above-identified range, the wet wipe may be oversaturated and soggy and the solution may pool in the bottom of the container.

In a particular aspect, wherein the wet wipes are individually packaged in a foil pouch, the preferred ratio of solution to dry weight of the wipe is from about 3.5:1 to about 6:1, more preferably from about 3.5:1 to about 5.2:1 and most preferably from about 4.7:1 solution to wipe based on dry weight of said wet wipe.

The solution in the wet wipe of the present invention comprises witch hazel, which is an effective cleansing agent and contributes a soothing, cooling and distinctive fragrance to the solution of the present invention. The amount of witch hazel present in the solution varies in a range from about 10 to about 50 percent, more preferably in a range from about 10 to about 20 percent, and most preferably about 20 percent, based on a total weight of the solution. In a particular embodiment, the present invention comprises witch hazel or hamamelis water as a suitable cleaning agent, commercially available from American Distilling Inc. and having an alcohol content of 14%.

To provide improved tactile properties and cleaning efficacy without excessive foaming or skin irritation, the solution in the wet wipes of the present invention comprises an amphoteric or zwitterionic surfactant. The betaine family of zwitterions possesses the positive-negative head group structure of trimethyl glycine (betaine), an amino acid derived from sugar beets. The hydrophobic tail group can be a straight chain alkyl group (such as in coco betaine), or can contain an amido group, such as cocamidopropyl betaine. Other betaines include lauramidopropyl betaine, oleamidopropyl betaine, ricinoleamidopropyl betaine, cetyl betaine and dimer dilinoleamidopropyl betaine. Additional variants are sulfobetaines, hydroxysulfobetaines and sultaines. Betaines are more resistant to thickening via addition of salts than their anionic cousins. For this reason, in order to achieve a pleasingly thick product, addition of viscosity-boosting polymeric additives may be necessary, which can increase the cost and complexity of the formula (see http://www.naturallycurly.com/curlreading/ ingredients/zwitterionic-surfactants-a-milder-alternative).

To provide the improved tactile and cleansing properties to the wet wipe of the present invention without excessive foaming or skin irritation, the solution of the present invention comprises at least one surfactant, preferably a betaine surfactant. The solution may include any amount of the betaine surfactant which provides the desired properties. The specific betaine selected can have a significant impact upon the viscosity, foaming behavior and detergency of the final product. In a particular embodiment, the solution includes from about 0.01 to about 10 weight percent and desirably from about 0.01 to about 5 weight percent of the betaine surfactant based on a total weight of the solution. Most preferably, the present invention comprises a capryl/capramidopropyl betaine, sold under the tradename TEGO® Betain 810, commercially available from Evonik Degussa, in a range of about 0.1 w/w % based on a total weight of the solution. Solutions having a less than the preferred surfactant weight percent ratios can be undesirable because of undesirable tactile properties such as tackiness and loss of silky after feel, reduced detersive activity and increased skin irritation.

The solution contained within the wet wipes of the present invention defines a pH from about 5 to about 7 and desirably from about 5 to about 6. A pH level below about 5 is generally undesirable because of potential skin irritation. Whereas, a pH level greater than about 7 is also undesirable due to possible compromising of preservative activity and can lead to skin irritation. Suitable buffers, such citric acid and sodium citrate, can be employed to relative amounts to achieve the desired pH. The solution of the present invention comprises a buffer system of about from 0.05 to about 0.25 weight percent of said solution.

The solution may also comprise a variety of other components which may assist in providing the desired wiping and cleaning properties. For example, the components may include water, emollients, at least one surfactant, at least one preservative, at least one chelating agent, at least one pH buffer, at least one fragrance or combinations thereof. The solution may also contain at least one lotion and/or medicament. To provide reduced skin irritation, the solution desirably includes at least from about 30 weight percent to about 80 weight percent of added purified water based on a total weight of the solution, more preferably about 63 weight percent of added purified water based on a total weight of the solution.

For example, the solution may include an effective amount of at least one preservative to inhibit the growth of microorganisms. Suitable preservatives are well known to those skilled in the art and may include, for example, parabens, sodium hydroxymethylglycinate, organic acids such as benzoic and malic acid, DMDM hydantoin and the like and combinations thereof. In a particular embodiment, the antimicrobial preservative comprises methylparaben, propylparaben and diazolidinyl urea which is commercially available from ISP Technologies, Inc. under the trade designation GERMALL II. The solution may include any amount of the preservatives which provides the desired antimicrobial effect. For example, the solution may include from about 0.1 to about 0.5 weight percent of the antimicrobial preservative based on a total weight of the solution, preferably 0.40 weight percent on a total weight of the solution.

Applicants have discovered that, when compared to conventional wet wipes which have included other types of surfactants, the wet wipes according to the different aspects of the present invention which comprise a betaine surfactant have improved tactile properties and cleaning efficacy without excessive levels of skin irritation. The solution may further include additional surfactants which can act as an emulsifier or provide additional cleansing properties. Suitable cosurfactants include, for example, anionic surfactants such as acyl glutamates and acyl isethionates, alkanolamides, amphoteric surfactants, nonionic surfactants and the like or combinations thereof. For example, a suitable acyl glutamate anionic surfactant is potassium cocoyl glutamate, a suitable acyl isethionate anionic surfactant is ammonium cocoyl isethionate, and suitable amphoteric surfactants include disodium capryloamphodipropionate and disodium cocoamphodiacetate. Suitable nonionic surfactants include diethanolamides having an average of from 12 to 16 carbon atoms, alkylphenol ethoxylates, alcohol ethoxylates, sorbitan esters, glycerol esters and the like. The solution may include any amount of the cosurfactant which provides the improved cleaning or tactile properties. For example, the solution may include from about 0.01 to about 5 weight percent of the cosurfactant based on a total weight of the solution. The present invention, in its most preferred embodiment, does not comprise the presence of co-surfactants in order to limit the irritation potential.

Moreover, the wet wipes of the present invention desirably exhibit low levels of foaming for improved performance. The wet wipes also exhibit a lubricious, silky feeling to the user for improved consumer acceptance.

The present invention comprises at least one suitable emollient or a combination of suitable emollients, such as botanical butters, vitamin E acetate, and aloe vera. The present invention comprises at least one emollient individually in a range of from about 0.01 percent to about 2 percent, more preferably individually in a range from about 0.01 percent to about 1.8 percent, and most preferably individually about 1.5 percent emollient wherein the weight percent is based on a total weight of said solution of the present invention. Preferably, the emollient is a vitamin derivative, most preferably vitamin E acetate.

Applicants have discovered that the use of an ethoxylated shea butter emollient, preferably the PEG-75 ethoxylated shea butter glyceride, serves multiple functions of providing emolliency, emulsification, and of co-solubilizing at least one additional emollient, preferably vitamin E acetate, which is well known in the art to be water-insoluble. Preferably, the emulsifier of the present invention is a botanical butter, more preferably an ethoxylated botanical butter, and most preferably an ethoxylated shea butter. In a preferred embodiment of the present invention, the solution comprises PEG-75 ethoxylated shea butter, commercially available from Aarhuskarlshamn under the trade name of Lipex 102 E-75®, as a most preferred emulsifier. The present invention comprises at least one emulsifier individually in a range of from about 0.01 percent to about 2 percent, more preferably individually in a range from about 0.01 percent to about 1.8 percent, and most preferably individually about 1.5 percent emulsifier wherein the weight percent is based on a total weight of said solution of the present invention.

During manufacture of the solution of the present invention, the ethoxylated shea butter glyceride is melted at 50 degrees C. in a separate side-phase mixing vessel. The vitamin E acetate is added to this side-phase vessel and dissolved in the ethoxylated shea butter glycerides with mixing. This side phase is then added to the main batch which is at ambient room temperature (about 25 degrees C.) with vigorous mixing of the main batch. The ethoxylated shea butter glycerides/vitamin E acetate phase is added as the second to last ingredient addition. If the ethoxylated shea butter glyceride and vitamin E acetate were to be added to the main batch as separate, independent additions (instead of manufacturing the side phase), the vitamin E acetate would not be solubilized in the main batch; when mixing is terminated, the vitamin E acetate will rise to the top of the solution as an oil. Once the ethoxylated shea butter/vitamin E acetate phase is added, then the propylene glycol preservative phase (containing the propylene glycol, parabens and the fragrance) is added and mixed at ambient temperature for approximately 15 minutes.

Additional emulsifiers, preferably mild emulsifiers, such as polysorbate 20 and other ethoxylated botanical butters may be employed in the solution of the present invention, in the range of from about 0.1 to about 2 weight percent, wherein the weight percent is based on a total weight of said solution.

The present invention comprises glycerin to improve the smoothness, to provide lubrication and as a humectant. Essential oils and botanical extracts can be added for fragrance. The present invention comprises the use of at least one fragrance to help convey a sense of freshness and scent pleasurable to one's olfactory senses. Fragrances derived from botanical extracts such as cucumber and chamomile, along with various fragrances, such as Bell Fragrances®, commercially available from the Bell Fragrances Corporation, may be employed in the present invention. The amount of at least one fragrance may range from about 0.05 weight percent to about 0.3 weight percent each wherein the weight percent is based on a total weight of said solution.

The present invention further comprises at least one chelating agent designed to protect the structural integrity and fragrance of the botanical extracts from unnecessary and unwanted iron which the solution may be exposed to during manufacturing. The presence of chelating agents may range from about 0.01 to about 0.1 weight percent, wherein the weight percent is based on a total weight of said solution. Preferred chelating agents of the present invention are edetate disodium, commercially available from Dow Chemical Company.

The wet wipes of the different aspects of the present invention may be manufactured using several different processes well known to those skilled in the art. The particular method and sequence of steps described herein is not a limitation to the present invention, but is disclosed only as one method of producing a wet wipe and stack of wet wipes. Initially, a supply roll of the material being converted into the wet wipes is unwound to provide a continuously moving web of material. The web of material is saturated or otherwise impregnated with the solution of the present invention by any suitable means such as spraying, dipping, or the like as are well known to those skilled in the art.

The web of material is slit in the machine direction into multiple ribbons, each of which may be folded into the type of fold desired for the individual wet wipe. The web of material is slit using a cutter as are well known to those skilled in the art. For example, the web of material can be slit into a pre-determined number of individual ribbons. The ribbons of material are then folded into a folded configuration such as a z-folded configuration. For example, each ribbon of material may define a top flap portion, a central portion and a bottom flap portion. The top and bottom flap portions are connected to and folded over and under the central portion, respectively to provide the z-folded configuration.

Each folded ribbon may then be combined, one ribbon on top of the other, with the other pre-determined number of folded ribbons from the same web of material to form a continuous towel. The towel is then cut into "clips" of wet wipes and the clips of wet wipes are arranged in a stacked configuration. The number of clips in a stack depends on the desired number of stacks and the number of wet wipes, such as 48 or 60 individual wet wipes, in the final package. The wet stacks are periodically weight checked, to assure the solution add-on is correct. If not, the solution add-on is adjusted. After the stack of wet wipes is property configured, it may be overwrapped, preferably with a plastic wrap, and then placed in the interior of a container, such as a plastic tub, to provide a package of wet wipes. The container provides a substantially hermetically sealed environment for the wet wipes to minimize the escape of any solution therefrom.

With respect to the manufacturing process for the individual wipe wrapped in a foil pouch, the pre-cut (preferably 5 inches by 6 inches), dry wipe is placed in the pouch and then the solution of the present invention is added to the pouch. The ratio of solution to dry wipe is greater in the pouch because there is some solution pooling in the pouch.

Accordingly, the different aspects of the present invention can advantageously provide wet wipes which, when compared to conventional wet wipes, have improved tactile properties and cleaning while maintaining low levels of skin irritation and foaming. Such wet wipes can advantageously be used for application to a woman's anal-rectal and perineal area, which, when compared to conventional wet wipes, have improved cleaning efficacy without excessive skin irritation or foaming and convey a sense and smell of freshness. Additional uses may comprise baby wipes, hand wipes, face wipes, cosmetic wipes, household wipes, industrial wipes and the like.

EXAMPLES

The following examples are presented to provide a more detailed understanding of the invention. The particular materials and parameters are exemplary and are not intended to limit the scope of the invention.

Example 1

A particularly suitable solution for the wet wipes of the present invention was prepared according to the following formulation:

This formula is described as a clear solution, which contains 20% w/w Witch Hazel as the active ingredient. The final product is a white, moist wipe saturated with this solution.

| Active Ingredients | | |
|---|---|---|
| Component Name/Commercially available from Vendor | % w/w | Label Designations (LD) |
| Witch Hazel USP (14% Alcohol)/ American Distilling Inc. Alcohol, 14.0-15.0% | 20.0 | Witch Hazel[1] |

| Inactive Ingredients | | |
|---|---|---|
| Component Name/Vendor | % w/w | Label Designations (LD) |
| Water Purified USP/Manufacturing Site | 63[2] | Purified Water |
| Glycerin USP, 96%/The Procter & Gamble Company, Cincinnati, OH | 9.0 | Glycerin |
| Propylene Glycol USP/The Dow Chemical Company, Midland, MI | 5.0 | Propylene Glycol |
| PEG 75 Shea Butter, Ethoxylated, Lipex 102 E-75/Aarhuskarlshamn | 1.5 | PEG 75 Shea Butter Glycerides (emollient and co-solubilizer) |
| Cucumber Extract,/Medallion International Inc. Cucumber Extract, 44.4% Propylene Glycol, 50.0% Water, 5.0% NEOLONE™ PE (preservative), 0.6% | 0.2 | N/A *Cucumis Sativus* (Cucumber) Fruit Extract Propylene Glycol Purified Water |
| Chamomile Extract/Medallion International Inc. Chamomile Extract, 39.0% Propylene Glycol, 50.0% Water. 10.0% DMDM Hydantoin (preservative), 1.0% | 0.2 | N/A *Chamomilla Recutita* (*Matricaria*) Flower Extract Propylene Glycol Purified Water DMDM Hydantoin |
| Germall II (Diazolidinyl Urea)/ISP Technologies, Inc. | 0.2 | Diazolidinyl Urea |
| Methylparaben NF/Ueno Fine Chemicals Industry, Ltd | 0.2 | Methylparaben |
| TEGO® Betaine 810/Evonik Degussa | 0.1 | Capryl/Capramidopropyl Betaine |
| Aloe Vera Gel/Concentrated Aloe Inc. *Aloe Barbadensis* Leaf Juice Potassium Sorbate Sodium Benzoate | 0.1 | N/A *Aloe Barbadensis* Leaf Juice N/A N/A |
| Vitamin E Acetate USP-FCC;/DSM Nutritional Products Ltd | 0.1 | Vitamin E Acetate |
| Citric Acid USP Anhydrous Granular/Archer Daniels Midland Company | 0.09 | Anhydrous Citric Acid |
| Sodium Citrate USP Hydrous/Archer Daniels Midland Company | 0.09 | Sodium Citrate |
| Edetate Disodium USP (VERSENE™ NA); VERSENE NA CHELATING AGENT/The Dow Chemical Company | 0.05 | Edetate Disodium |
| Fragrance/Bell Flavors and Fragrances/Bell Fragrances Corporation Polysorbate 20, >50% Dipropylene Glycol, 10-20% Synthetic Aromatics, 25-50% | 0.05 | N/A Polysorbate 20 Dipropylene Glycol Fragrance |
| Propylparaben NF/Ueno Fine Chemicals Industry, Ltd | 0.05 | Propylparaben |

Endnotes
[1] Witch Hazel USP contains 14.5% v/v alcohol. The alcohol content of the formulation is from about 2.8 to about 3.0% w/w, which is contributed entirely by the witch hazel component.
[2] Purified water is employed as rinse water and as a direct addition. In all cases, the rinse water is subsequently added to the main mixing vessel.

Example 2

A suitable solution for the wet wipes of the present invention was prepared according to the following formulation:

The amount of witch hazel was increased to 50 w/w % and the amount of water was reduced to about 33 w/w %.

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A wet wipe for cleansing skin comprising a fibrous sheet material and an aqueous-based formulation which comprises:
   a.) from about 10 to about 50 weight percent witch hazel;
   b.) from about 0.01 to about 2 weight percent ethoxylated shea butter; and
   c.) from about 0.01 to about 2 weight percent vitamin E acetate;

wherein the weight percent is based on a total weight of said formulation; and wherein said formulation is prepared by:
i) forming a side-phase by
(a) melting the ethoxylated shea butter at 50 degrees C. in a side-phase mixing vessel;
(b) adding the vitamin E acetate to the side-phase mixing vessel; and
(c) mixing the ethoxylated shea butter and the vitamin E acetate in the side-phase mixing vessel; and
ii) mixing the side-phase to a main batch at 25 degrees C. with vigorous mixing.

2. The wet wipe according to claim 1 wherein said wet wipe comprises from about 10 to about 90 weight percent of said formulation based on a dry weight of said wet wipe.

3. The wet wipe according to claim 1 wherein said wet wipe comprises from about 4:1 formulation to wipe based on dry weight of said wet wipe.

4. The wet wipe according to claim 1 wherein the formulation comprises a ratio of ethoxylated shea butter to vitamin E acetate of about 10:1.

5. The wet wipe according to claim 1 wherein the formulation comprises about 1.5% ethoxylated shea butter, wherein the weight percent is based on a total weight of said solution.

6. The wet wipe according to claim 1 wherein the formulation comprises at least one surfactant, wherein the at least one surfactant is capryl/capramidopropyl betaine.

7. The wet wipe according to claim 1 wherein the formulation further includes from about 0.1 to about 0.5 weight percent based on a total weight of said formulation of at least one antimicrobial preservative, wherein the antimicrobial preservative comprises diazolidinyl urea, propylparaben, and methylparaben.

8. The wet wipe according to claim 1 wherein the formulation has a pH of from about 5 to about 7.

9. The wet wipe according to claim 1 wherein said formulation further comprises from about 0.01 to about 10 weight percent glycerin based on a total weight of said formulation.

10. The wet wipe according to claim 1 said formulation further comprises from about 0.01 to about 0.5 weight percent botanical extracts based on a total weight of said formulation.

11. The wet wipe according to claim 1 wherein the formulation comprises about 20 weight percent witch hazel based on a total weight of said formulation.

12. The wet wipe of claim 1, wherein said aqueous-based formulation comprises:
a.) about 50 weight percent witch hazel;
b.) about 9 weight percent glycerin;
c.) about 5 weight percent propylene glycol;
d.) about 1.5 weight percent ethoxylated shea butter;
e.) about 0.2 weight percent cucumber extract;
f.) about 0.2 weight percent chamomile extract;
g.) about 0.2 weight percent diazolidinyl urea;
h.) about 0.2 weight percent fragrance;
i.) about 0.2 weight percent methylparaben;
j.) about 0.1 weight percent capramidopropyl betaine;
k.) about 0.1 weight percent aloe vera;
l.) about 0.1 weight percent vitamin E actetate;
m.) about 0.09 weight percent citric acid;
n.) about 0.09 weight percent sodium citrate;
o.) about 0.05 weight percent edetate disodium;
p.) about 0.05 weight percent propylparaben; and
q.) about 33 weight percent added purified water; based on a total weight of said formulation.

13. The wet wipe of claim 1, wherein said aqueous-based formulation comprises:
a.) about 20 weight percent witch hazel;
b.) about 9 weight percent glycerin;
c.) about 5 weight percent propylene glycol;
d.) about 1.5 weight percent ethoxylated shea butter;
e.) about 0.2 weight percent cucumber extract;
f.) about 0.2 weight percent chamomile extract;
g.) about 0.2 weight percent diazolidinyl urea;
h.) about 0.2 weight percent fragrance;
i.) about 0.2 weight percent methylparaben;
j.) about 0.1 weight percent capramidopropyl betaine;
k.) about 0.1 weight percent aloe vera;
l.) about 0.1 weight percent vitamin E actetate;
m.) about 0.09 weight percent citric acid;
n.) about 0.09 weight percent sodium citrate;
o.) about 0.05 weight percent edetate disodium;
p.) about 0.05 weight percent propylparaben; and
q.) about 63 weight percent added purified water; based on a total weight of said formulation.

14. A method of cleansing a skin area of a subject comprising wiping the skin area with the wet wipe according to claim 1.

15. A method of cleansing a skin area of a subject comprising wiping the skin area with the wet wipe according to claim 12.

16. A method of manufacturing a wet wipe for cleansing skin comprising adding an effective amount of an aqueous based formulation to a fibrous sheet material, wherein the aqueous based formulation comprises:
a.) from about 10 to about 50 weight percent witch hazel;
b.) from about 0.01 to about 2 weight percent ethoxylated shea butter; and
c.) from about 0.01 to about 2 weight percent vitamin E acetate;
wherein said formulation is prepared by:
i) forming a side-phase by
(a) melting the ethoxylated shea butter at 50 degrees C. in a side-phase mixing vessel;
(b) adding the vitamin E acetate to the side-phase mixing vessel; and
(c) mixing the ethoxylated shea butter and the vitamin E acetate in the side-phase mixing vessel; and
ii) mixing the side-phase to a main batch at 25 degrees C. with vigorous shaking.

17. The method of claim 16, wherein said aqueous-based formulation comprises:
a.) about 20 weight percent witch hazel;
b.) about 9 weight percent glycerin;
c.) about 5 weight percent propylene glycol;
d.) about 1.5 weight percent ethoxylated shea butter;
e.) about 0.2 weight percent cucumber extract;
f.) about 0.2 weight percent chamomile extract;
g.) about 0.2 weight percent diazolidinyl urea;
h.) about 0.2 weight percent fragrance;
i.) about 0.2 weight percent methylparaben;
j.) about 0.1 weight percent capramidopropyl betaine;
k.) about 0.1 weight percent aloe vera;
l.) about 0.1 weight percent vitamin E acetate;
m.) about 0.09 weight percent citric acid;
n.) about 0.09 weight percent sodium citrate;
o.) about 0.05 weight percent edetate disodium;
p.) about 0.05 weight percent propylparaben; and
q.) about 63 weight percent added purified water; based on a total weight of said formulation.

18. The method of claim 16, wherein said aqueous-based formulation comprises:
   a.) about 20 weight percent witch hazel;
   b.) about 9 weight percent glycerin;
   c.) about 5 weight percent propylene glycol;
   d.) about 1.5 weight percent ethoxylated shea butter;
   e.) about 0.2 weight percent cucumber extract;
   f.) about 0.2 weight percent chamomile extract;
   g.) about 0.2 weight percent diazolidinyl urea;
   h.) about 0.2 weight percent fragrance;
   i.) about 0.2 weight percent methylparaben;
   j.) about 0.1 weight percent capramidopropyl betaine;
   k.) about 0.1 weight percent aloe vera;
   l.) about 0.1 weight percent vitamin E acetate;
   m.) about 0.09 weight percent citric acid;
   n.) about 0.09 weight percent sodium citrate;
   o.) about 0.05 weight percent edetate disodium;
   p.) about 0.05 weight percent propylparaben; and
   q.) about 63 weight percent added purified water;
   based on a total weight of said formulation.

* * * * *